United States Patent [19]
Steiner et al.

[11] Patent Number: 5,874,604
[45] Date of Patent: Feb. 23, 1999

[54] PROCESS FOR PREPARING ALKYL HALOSILANES

[75] Inventors: Matthias-Sven Steiner, Leverkusen; Bruno Degen, Much; Rainer Weber, Odenthal, all of Germany

[73] Assignee: GE Bayer Silicones GmbH & Co. Kg, Erkrath, Germany

[21] Appl. No.: 955,674

[22] Filed: Oct. 22, 1997

[30] Foreign Application Priority Data

Nov. 4, 1996 [DE] Germany .................. 196 45 359.3

[51] Int. Cl.$^6$ ....................................................... C07F 7/16
[52] U.S. Cl. ............................................................. 556/472
[58] Field of Search ................................................. 556/472

[56] References Cited

U.S. PATENT DOCUMENTS

| | | |
|---|---|---|
| Re. 33,452 | 11/1990 | Ward, III et al. . |
| 2,380,995 | 8/1945 | Rochow et al. . |
| 4,218,387 | 8/1980 | Maas et al. ............... 556/472 UX |
| 4,450,282 | 5/1984 | Ritzer et al. ............... 556/472 |
| 4,487,950 | 12/1984 | Ward et al. ............... 556/472 |
| 4,504,597 | 3/1985 | Klar et al. ............... 502/343 |
| 4,520,130 | 5/1985 | Hashiguchi et al. ............... 502/345 |
| 4,602,101 | 7/1986 | Halm et al. . |
| 4,762,940 | 8/1988 | Halm et al. . |
| 4,946,978 | 8/1990 | Halm et al. . |
| 5,015,751 | 5/1991 | Feldner et al. . |
| 5,049,343 | 9/1991 | Sorensen . |
| 5,059,706 | 10/1991 | Degen et al. ............... 556/472 |
| 5,258,053 | 11/1993 | Forwald et al. . |
| 5,334,738 | 8/1994 | Pachaly et al. . |
| 5,500,399 | 3/1996 | Faure et al. . |
| 5,605,583 | 2/1997 | Margaria . |

FOREIGN PATENT DOCUMENTS

| | | |
|---|---|---|
| 0391133 | 10/1990 | European Pat. Off. . |
| 0620226 | 10/1994 | European Pat. Off. . |
| 3501085 | 8/1985 | Germany . |
| 2 153 697 | 8/1985 | United Kingdom . |
| WO 94/00799 | 1/1994 | WIPO . |

OTHER PUBLICATIONS

"Organohalosilanes—Precusors to Silicones", Elsevier New York 1967, p. 129.

*Primary Examiner*—Paul F. Shaver
*Attorney, Agent, or Firm*—Sprung Kramer Schaefer & Briscoe

[57] ABSTRACT

The present invention relates to a process for preparing alkyl halosilanes by reacting a contact material which comprises, in addition to silicon, at least one copper-containing compound as catalyst and at least one promoter, with an alkyl halide.

7 Claims, No Drawings

PROCESS FOR PREPARING ALKYL HALOSILANES

The present invention relates to a process for preparing alkyl halosilanes by reacting a contact material which comprises, in addition to silicon, a copper-containing compound as catalyst and at least one promoter, with an alkyl halide.

BACKGROUND OF THE INVENTION

The basic process for preparing methyl chlorosilanes is the direct reaction of milled silicon with methyl chloride in the presence of copper as catalyst. The reaction is known to a person skilled in the art as the "Rochow synthesis" and is described in U.S. Pat. No. 2,380,995.

According to this process, a mixture of methyl chlorosilanes in which dichlorodimethylsilane (Di) is the main constituent is formed. In addition, methyl trichlorosilane (Tri) and other products such as, for instance, trimethyl chlorosilane (mono), tetramethyl silane (TMS), methyl hydrogen dichlorosilane (MeH) and higher boiling methylchlorodisilanes (PS) are formed.

Since the discovery of this synthesis, efforts have been made to improve the performance of the synthesis and to increase the proportion of dichlorodimethylsilane.

This is achieved in particular by using purer raw materials and by the use of promoters. Suitable promoters, according to U.S. Pat. No. 4,602,101, are zinc, tin and phosphorus, as the elements or in the form of their compounds. U.S. Pat. No. 5,059,706 also discloses, in addition to zinc and optionally tin, the use of volatile phosphorus compounds as promoters. At high phosphorus concentrations, although acceptable selectivities with respect to dichlorodimethylsilane are obtained, the yields are unsatisfactory.

The object of the present invention was, therefore, the provision of a process for preparing alkyl chlorosilanes which has a high selectivity and a high yield.

SUMMARY OF THE INVENTION

It has now been found that high yields and good selectivities are achieved by specific copper-containing catalysts together with at least one phosphorus compound which is liquid or gaseous at room temperature as promoter.

DETAILED DESCRIPTION OF THE INVENTION

The present invention therefore provides a process for preparing alkyl halosilanes by reacting a contact material which comprises, in addition to silicon, at least one copper-containing compound as catalyst and at least one promoter, with an alkyl halide, wherein a compound of the formula I

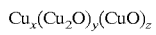
$$Cu_x(Cu_2O)_y(CuO)_z \qquad (I)$$

where x+y+z=1,
which has a BET surface area of 0.05 to 1.0 m²/g and an average particle diameter between 1 and 200 μm, preferably less than 100 μm, in particular between 10 and 80 μm, is used as a copper-containing compound and a phosphorus compound which is liquid or gaseous at room temperature is used as promoter.

The BET surface area was determined with a Micrometrics Flow-Sorb 2/2300 using $N_2$.

The average particle diameter was determined with a Malvern Master Sizer by means of laser diffraction.

In a preferred embodiment of the invention, x=0 to 0.3 and x+y+z=1 in these catalysts used.

The catalyst used, therefore, preferably has the following indices:
x=0–0.3, particularly preferably 0–0.2,
y=0.2–0.9, particularly preferably 0.4–0.8 and
z=0.1–0.6, particularly preferably 0.3–0.5,
wherein the sum of x+y+z is always 1.

The copper-containing compound may be doped with up to 3000 ppm of each of tin, zinc, aluminium, iron, antimony, arsenic, phosphorus, alkali metals and/or alkaline earth metals, in their elemental form or in the form of their compounds.

The copper-containing compound used can be prepared by atomizing molten metallic copper optionally together with other molten metals in a receiving medium having a temperature which is lower than the temperature of the copper, isolating the solified copper particles and oxidizing them. The receiving medium can be i.e. water and/or oil.

Phosphorus compounds which are liquid or gaseous at room temperature are understood to be those compounds which are liquid or gaseous at 20° to 30° C. and at a pressure of 1 atmosphere. Therefore compounds of the formula $PR_aX_b$, where a=0–3, b=3-a and X=H, F, Cl, Br and/or OR, $NR_2$, where $R=C_1$–$C_6$-alkyl, are preferably used.

The following are particularly preferred as a phosphorus compound: $PF_3$, $PCl_3$, $P(OR)_3$, where $R=C_1$–$C_6$-alkyl and/or $PH_3$. $PCl_3$ and/or $P(OMe)_3$ are quite particularly preferred.

In a preferred embodiment of the invention, the phosphorus compound is used in an amount of 20–2500 ppm. by weight of silicon.

The amount of copper-containing compound preferably amounts to 0.05 to 10 wt. %, preferably 0.1 to 7 wt. %, by weight silicon.

In a further embodiment of the invention, other known promoter substances are used as promoters in addition to the phosphorus compound. Preferred promoter substances are: zinc or zinc compounds, aluminium or aluminium compounds, tin or tin compounds, selenium or selenium compounds, tellurium or tellurium compounds, sulphur or sulphur compounds and indium or indium compounds, on their own or in combination.

Suitable compounds of the elements Zn, Al, Sn, Se, Te, S and/or In are, for example, oxides, halides, alloys, etc.

The promoter substances, if they are present, are preferably used in the following amounts:
tin: 5–200 parts per 1,000,000 parts of silicon and/or
zinc: 10–10,000 parts per 1,000,000 parts of silicon and/or
aluminium: 0.01–1 wt. %, with reference to silicon, and/or
selenium/tellurium: 20–2500 parts per 1,000,000 parts of silicon and/or
indium: 20–2500 parts per 1,000,000 parts of silicon.
sulphur: 5–2000 parts per 1,000,000 parts of silicon.
All promoter substances can also be present as compound.

The promoter substances Sn, Zn, Al, Se, Te, In and/or S may be alloyed with the silicon which is used (e.g. U.S. Pat. No. 5,049,343, U.S. Pat. No. 4,946,978, WO 94/00 799).

Tin, aluminium or zinc, individually or in combination, as elements or in the form of their compounds, are preferably used.

The silicon used in the context of the invention may be silicon with a purity of >95 wt. %. Silicon with a purity of >98 wt. % is preferred. The particle sizes of the silicon used may be selected to have any value at all, but are preferably between 50 and 500 μm.

The following may also be used as silicon: atomised silicon in accordance with U.S. Pat. No. 5,015,751 or also structurally optimised silicon in accordance with U.S. Pat. No. 5,334,738 or silicon prepared in accordance with U.S. Pat. No. 5,605,583 or U.S. Pat. No. 5,258,053.

Special types of silicon such as, for example, those described in U.S. Pat. No. 5,500,399 may also be used.

The alkyl halides used in the context of the invention are any common $C_1$–$C_8$ -alkyl halides, preferably methyl chloride.

Any copper catalyst commonly used in the Rochow synthesis may also be added to the copper-containing compound (catalyst), the following being mentioned by way of example: partially oxidised copper ($Cu^o$/$Cu_2O$/CuO) (U.S. Pat. No. 4,500,724), mixtures of metallic copper and $Cu_2O$/CuO (GB-A 2 153 697), $Cu_2Cl_2$, $CuCl_2$ (U.S. Pat. No. 4,762,940), Cu formate (U.S. Pat. No. 4,487,950), etc. Partially oxidised copper with the constituents $Cu^o$, $Cu_2O$ and/or CuO is preferably used. Partially oxidised copper in this instance preferably has the following composition: $Cu^o$: 0 to 30 wt. %, $Cu_2O$: 30 to 90 wt. % and CuO: 10 to 60 wt. %, wherein the sum of all the constituents is 100%.

When adding further amounts of catalyst, the total amount of copper should not exceed 10 wt. %, by weight of silicon.

The process is conventionally performed within the temperature and pressure ranges commonly used for the Rochow synthesis.

A temperature between 280° and 390° C. and a pressure of 1 to 10 bar are preferred.

The contact material used is defined as a physical mixture of silicon and copper and/or at least one copper-containing compound as catalyst and at least one promoter.

This contact material may be introduced to the reactor for reaction untreated or it may be partially or completely pretreated or preformed in an appropriate process. These types of process are described, for example, in Voorhoeve: "Organohalosilanes—Precursors to Silicones", Elsevier New York 1967, p. 129.

The process according to the invention is also not restricted to specific process engineering during direct synthesis. Thus, the reaction may be performed batchwise or continuously and it may be conducted in either a fluidised bed or a stirred bed or in a fixed bed.

The liquid or gaseous phosphorus compound is preferably added to the methyl chloride stream.

The following examples are intended to illustrate the invention in more detail, without, however, restricting it in any way (%-age data are wt. %).

WORKING EXAMPLES

The following experiments were performed in a stirred bed reactor made of glass, internal diameter=30 mm, which was fitted with a spiral stirrer. Silicon with a purity of at least 98.8% and an average particle diameter of 71 to 160 μm was used.

The contact material consisted of 40 g of silicon, 3.2 g of copper catalyst (($Cu_{0.2}(Cu_2O)_{0.63}$ $(CuO)_{0.17}$, BET-surface 0,47 $m^2$/g tin content 460 ppm prepared by atomizing molten copper and tin in water with a pressure of 300 bar, isolating them and oxidizing them afterwards, and 0.05 g of ZnO and was homogenised before use.

Methyl chloride was passed, from below, through the contact material at a pressure of 2 bar, via a glass frit. The throughput of methyl chloride was maintained at a constant value and was in all cases about 1.8 l/h. After passing through an induction phase, a steady-state test phase was set up at 330° C. The amount of crude silane produced per time unit was determined under these conditions. The individual constituents were determined by gas chromatography.

The values cited are each average values from four separate determinations, each test being reproduced at least once. All data referring to amounts are given with reference to the silicon used.

Example 1

This example shows the effect of adding $PCl_3$ to the MeCl feed. The silicon used here has the following constituents: Al: 0.19%; Ca: 0.073%; Mg: 5 mg/kg; Fe: 0.46%, Ti: 0.022%, P, Zn, Cu, Ni, Cr, V (their total) <27 mg/kg, Pb, Sn<1 mg/kg. The amounts weighed out and the results are given in Table 1 below.

TABLE 1

| Test | Added P [ppm] | Rate of prod. [g/h] | Di[1] [%] | Tri/Di[1] |
|---|---|---|---|---|
| 1 | 0 | 11.0 | 91.6 | 0.042 |
| 2 | 100 | 11.5 | 92.0 | 0.039 |
| 3 | 200 | 11.3 | 92.4 | 0.040 |

[1])Di: dichlorodimethylsilane $Me_2SiCl_2$; Tri/Di: (trichloromethylsilane $MeSiCl_3$/dichlorodimethylsilane $Me_2SiCl_2$); percentage data (wt. %) are given with reference to the monomers produced.

This shows that adding phosphorus in the form of $PCl_3$, combined with the copper catalyst, to the contact material produced improved selectivity and increased yields.

Example 2

This example shows a comparison with another conventional catalyst according to U.S. Pat. No. 4,520,130. The silicon used contained the following main co-components: Al: 0.18%, C: 0.032%; Fe: 0.38%, Ti: 0.024%, P, Zn, Cu, Ni, Cr, V<30 ppm, Pb, Sn:<1 ppm. The conventional catalyst had the following characteristic values: $Cu_{0.23}(Cu_2O)_{0.45}$ (CuO)0.32, BET surface area: 2.0 $m^2$/g, Sn: 110 ppm. The starting quantities and the results are shown in the following Table 2:

| Example No. | Catalyst | Quantity of P added [in ppm] | Rate of production [g/h] | Di [%][1] | Tri/Di[1] |
|---|---|---|---|---|---|
| 1 | according to the invention | 0 | 10.3 | 91.9 | 0.042 |
| 2 | conventional | 0 | 9.9 | 87.6 | 0.076 |
| 3 | according to the invention | 100 | 10.4 | 92.3 | 0.040 |
| 4 | conventional | 100 | 9.2 | 88.8 | 0.071 |

[1])Di: dichlorodimethylsilane $Me_2SiCl_2$; Tri/Di: (trichloromethylsilane $MeSiCl_3$/dichlorodimethylsilane $Me_2SiCl_2$); percentage data (wt. %) are given with reference to the monomers produced.

This shows that when the catalyst according to the invention is used both the rate of production and the selectivity in relation to dimethyldichlorosilane (Di) can be increased by adding $PCl_3$, whereas a conventional catalyst is adversely affected in relation to yield.

We claim:

1. Process for preparing alkyl halosilanes by reacting a contact material comprising silicon, at least one copper-containing compound as catalyst and at least one promoter, with an alkyl halide, wherein said copper-containing compound is a compound of the formula I $$Cu_x(Cu_2O)_y(CuO)_z \quad (I)$$

where x+y+z=1,
in the form of particles having an average BET surface area between 0.05 and less than 1.0 m$^2$/g and an average particle diameter between 1 and 200 μm and wherein a phosphorus compound which is liquid or gaseous at room temperature is used as promoter.

2. A process according to claim 1, wherein a compound of formula (I) in which x=0–0.3, y=0.2–0.9 and z=0.1–0.6 and x+y+z=1, is used.

3. Process according to claim 1, wherein PF$_3$, PCl$_3$, PBr$_3$, P(OR)$_3$, where R is a C$_1$–C$_6$-alkyl group, PH$_3$ or a combination thereof is used as phosphorus compound.

4. Process according to claim 1, wherein the phosphorus compound is used in an amount of 20–2500 ppm. by weight of silicon.

5. Process according to claim 1, wherein the copper-containing compound is used in an amount of 0.05 to 10 wt. %, by weight of silicon.

6. Process according to claim 1, wherein tin, zinc, selenium, tellurium, sulphur, aluminium or indium, individually or in combination with one or more of each other, in elemental form or in the form of their compounds, are used as further promoter substances.

7. Process according to claim 1, wherein methyl chloride is used as the alkyl halide.

* * * * *

UNITED STATES PATENT AND TRADEMARK OFFICE
CERTIFICATE OF CORRECTION

PATENT NO : 5,874,604
DATED : February 23, 1999
INVENTOR(S): Steiner, et al.

It is certified that error appears in the above-identified patent and that said Letters Patent is hereby corrected as shown below:

| | |
|---|---|
| Col. 2, line 10 | Delete " aluminium " and substitute -- aluminum -- |
| Col. 2, line 38 | Delete " aluminium or aluminium " and substitute -- aluminum or aluminum -- |
| Col. 2, line 50 | Delete " aluminium " and substitute -- aluminum -- |
| Col. 2, line 60 | Delete " aluminium " and substitute -- aluminum -- |
| Col. 6, line 9 | Delete " aluminium " and substitute -- aluminum -- |

Signed and Sealed this

Seventh Day of September, 1999

Attest:

Q. TODD DICKINSON

Attesting Officer

Acting Commissioner of Patents and Trademarks